United States Patent [19]

Weber et al.

[11] 4,115,569
[45] Sep. 19, 1978

[54] CYCLIC DIAMINE DERIVATIVES

[75] Inventors: Rolf-Ortwin Weber, Wiesbaden; Alfons Söder, Frankfurt, Main-Schwanheim; Istvan Boksay, Kiedrich, all of Germany

[73] Assignee: Hoechst Aktiengesellschaft, Frankfurt, Germany

[21] Appl. No.: 606,488

[22] Filed: Aug. 21, 1975

Related U.S. Application Data

[62] Division of Ser. No. 307,406, Nov. 17, 1972.

[30] Foreign Application Priority Data

Aug. 18, 1972 [DE] Fed. Rep. of Germany ....... 2240665
Nov. 19, 1971 [DE] Fed. Rep. of Germany ....... 2157424

[51] Int. Cl.$^2$ ................... A61K 31/495; C07D 295/10
[52] U.S. Cl. ........................... 424/250; 260/329 S; 260/329 HS; 260/329 F; 260/330.5; 260/332.2 R; 260/346.22; 424/275; 424/285; 544/365; 544/373; 544/364; 544/337; 544/379; 544/374; 544/376; 544/363
[58] Field of Search ....... 260/268 BC, 330.5, 332.2 R, 260/329 S, 329 HS, 329 F, 346.22; 424/250, 275, 285

[56] References Cited

U.S. PATENT DOCUMENTS 3,787,419  1/1974  Bruce ............................. 260/268 C Primary Examiner—Paul M. Coughlan, Jr.
Attorney, Agent, or Firm—Littlepage, Quaintance, Murphy, Richardson and Webner

[57] ABSTRACT

A compound having the general formula or an acid addition salt thereof

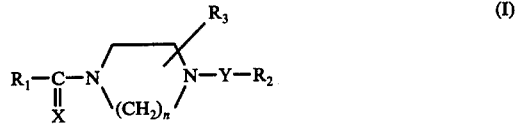

(I)

in which formula $R_1$ is selected from the group consisting of
  A. an at least mononuclear heterocyclic group having 4 to 10 carbon atoms in the ring system bound to the group

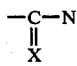

through a carbon atom and containing at least one oxygen, nitrogen or sulphur atom,
  B. substitution products of (A) containing at least one substituent selected from the group consisting of halogen, trifluoromethyl, hydroxy, alkoxy of 1 to 3 carbon atoms, unsubstituted amino, amino substituted by up to two alkyl groups each having 1 to 3 carbon atoms and alkyl groups having 1 to 6 carbon atoms, X is oxygen, sulphur or an NH-group, Y is an alkylene group having 1 to 3 carbon atoms in the chain, or an alkylene group having 1 to 3 carbon atoms in the chain substituted by (a) up to 3 alkyl groups each having up to 3 carbon atoms and a total of not more than 8 carbon atoms, or (b) substituted by one or two phenyl groups, $R_2$ is selected from the group consisting of
  C. an at least mononuclear carbocyclic or heterocyclic group having 4 to 10 carbon atoms in the ring system, containing but one heteroatom in a ring,
  D. substitution products of (C) containing at least one substituent selected from the group consisting of nitro, halogen, trifluoromethyl, alkyl having 1 to 6 carbon atoms, hydroxy, alkoxy having 1 to 3 carbon atoms, unsubstituted amino groups and amino groups substituted by up to two alkyl groups each having 1 to 3 carbon atoms, $R_3$ is hydrogen or up to two substituents selected from alkyl groups having up to 2 carbon atoms and phenyl groups.

$n$ is 2 or 3;

a process for its preparation and a pharmaceutical composition containing said compound (I).

6 Claims, No Drawings

CYCLIC DIAMINE DERIVATIVES

This is a division of application Ser. No. 307,406, filed on Nov. 17, 1972.

This invention is concerned with cyclic diamine derivatives.

Some monoacylated cyclic diamines and their chemotherapeutic activity are known. They have for example attained importance against parasites. Thus 4-methylpiperazinocarboxylic acid-(1)-diethylamide citrate has been successfully used against filaria and dictyocaulus infections, methyl-4-($\beta,\beta,\beta$-tris-(4-chlorophenyl)-propionyl)piperazine against infections of dicroecenium lanceatum and piperazino-1-dithiocarboxylic acid against ascarides.

One aspect of this invention provides a compound having the general formula

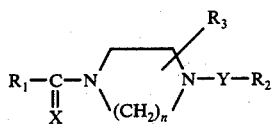 (I)

wherein
$R_1$ is a mono- or polynuclear saturated or unsaturated heterocyclic group having 4 to 10 carbon atoms in the ring system bound to the group

through a carbon atom and containing at least one oxygen, nitrogen or sulphur atom and being unsubstituted or substituted by one or more substituents selected from halogen, trifluoromethyl, hydroxy, alkoxy of 1 to 3 carbon atoms, amino being unsubstituted or substituted by one or two alkyl groups each having 1 – 3 carbon atoms each, and alkyl groups having 1 to 6 carbon atoms;
X is oxygen, sulphur or an NH-group;
Y is an alkylene group having 1 to 3 carbon atoms in the chain which may be substituted by up to 3 alkyl groups each having up to 3 carbon atoms and a total of not more than 8 carbon atoms, or substituted by one or two phenyl groups; $R_2$ is a mono- or polynuclear saturated or unsaturated carbocyclic or heterocyclic group having 4 to 10 carbon atoms in the ring system, containing but one heteroatom in a ring and being unsubstituted or substituted by one or more substituents selected from nitro, halogen, trifluoromethyl, alkyl having 1 to 6 carbon atoms, hydroxy, alkoxy having 1 to 3 carbon atoms and amino groups being unsubstituted or substituted by one or two alkyl groups each having 1 – 3 carbon atoms;
$R_3$ represents one or two optional substituents selected from alkyl groups having up to 2 carbon atoms and phenyl groups; and
$n$ is 2 or 3; and acid addition salts thereof.

These compounds are in particular interesting because of their psychotherapeutic action.

In the compounds of formula (I) $R_1$ can e.g. be a mononuclear 5- or 6-membered group with 4 or 5 C-atoms in the ring. Both mononuclear and polynuclear $R_1$ groups can have one or more of the above-indicated substituents. Suitable $R_1$ groups are for example furyl, dihydrofuryl, tetrahydrofuryl, benzofuryl, dihydrobenzofuryl, pyrryl, dihydropyrryl, tetrahydropyrryl, pyronyl, thienyl, benzothienyl, pyridyl, dihydropyridyl, piperidyl, quinolyl, dihydroquinolyl, tetrahydroquinolyl, isoquinolyl, dihydroisoquinolyl, and tetrahydroisoquinolyl groups; preferably however $R_1$ has the structure:

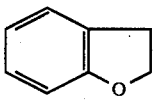 (IX)

According to a preferred embodiment of the invention Y is an unbranched alkylene group with 1 or 2 C-atoms or an alkylene, preferably methylene, group optionally substituted by one phenyl group.

The cyclic group $R_2$ can e.g. be aromatic or cycloaliphatic. If $R_2$ is a heterocyclic group it can for example be a 5- or 6-membered ring. Suitable $R_2$-Y groups are for example benzyl, cyclohexylmethyl, diphenylmethyl, phenylethyl e.g. 2-phenylethyl, 2-phenylpropyl, tetrahydronaphthylmethyl, indanylmethyl, furfuryl, tetrahydrofurfuryl, thenyl, quinolylmethyl or a pyridylmethyl group, any of which in turn can carry the above-indicated substituents.

In the $R_1$ and $R_2$ groups the amino groups of the substituents can be substituted by one or two alkyl groups with in each case up to 3 C-atoms. The alkoxy groups present as substituents can also contain up to 3 C-atoms. Both in the amine and in the alkoxy substituents the alkyl groups can be straight chained or branched.

Cyclic diamines according to the invention may be in the form of acid-addition salts with physiologically acceptable acids, e.g. monobasic acids such as hydrochloric acid, nitric acid, cyclohexylsulphamic acid, or polybasic acids e.g. phosphoric acid, sulphuric acid or citric acid.

According to a further aspect of the invention there is provided a process for the preparation of compounds of general formula (I) and acid addition salts thereof wherein:

a. a diamine of general formula

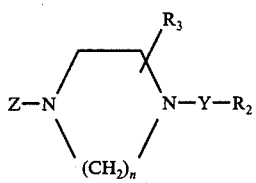 (III)

is reacted with a carboxylic or thiocarboxylic acid of the general formula

$R_1$—CX—OH (IV)

or carbamide or thiocarbamide - forming derivative thereof, wherein Y, $R_1$, $R_2$, $R_3$ and $n$ are as defined in claim 1, X is oxygen or sulphur and Z is hydrogen or, if a carboxylic or thiocarboxylic acid of general formula (IV) is employed, may be a phosphorus ester group, an acyl group of a phenoxycarbonyl group all activating carbamide bond formation; or b. a compound of general formula (I) wherein X is oxygen is reacted with a sulphur compound in a manner known per se for the conversion of amides to thioamides; or c. an amino-magnesium halide of general formula

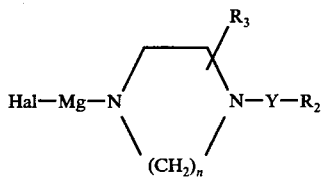 (V)

is reacted with a nitrile of the general formula $R_1—CN$ (VI) to form a compound of general formula (I) wherein X is an NH group, Hal in formula (V) being chlorine or bromine and Y, $R_1$ and $R_2$ being as defined in claim 1; or d. an N-monoacyldiamine of general formula

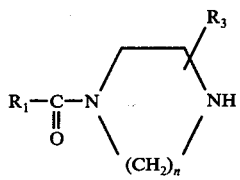 (VII)

is reacted with a carbocyclic or heterocyclic halide of the general formula $Hal-Y-R_2$ (VIII), the groups $R_1$, $R_2$, $R_3$, X, Y and n being as defined in claim 1; or e. a salt of a dithiocarbamic acid of general formula

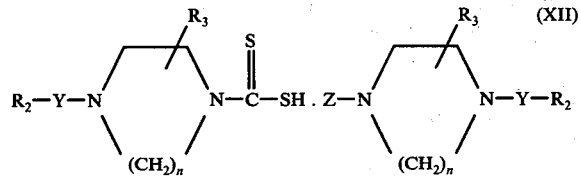 (XII)

wherein both $R_2$ groups, both $R_3$ groups, both Y groups and both $n$'s are the same, is reacted with a nitrile of the formula $R_1—CN$ (VI) at an elevated temperature to form a compound of general formula (I) in which X is sulphur, $R_1$, $R_2$, $R_3$, $n$ and Y being as defined in claim 1 and Z is hydrogen; or f. a dithiocarboxylic acid ester of general formula

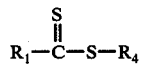 (XIV)

is reacted with a compound of general formula (III) above, $R_1$, $R_2$ and $R_3$ being as defined in claim 1, Z being hydrogen and $R_4$ being an alkyl radical having 2 to 18 carbon atoms or an aryl radical having 6 to 10 carbon atoms in the ring system and being unsubstituted or substituted, whereby ester aminolysis occurs with elimination of the mercaptan $R_4SH$ to form a compound of general formula (I) wherein X is sulphur.

According to (a), one may e.g. employ a carboxylic acid or thiocarboxylic acid of general formula (IV) in the presence of dehydrating substances promoting carbamide or thiocarbamide formation, or one may use a corresponding derivative of the acid (IV) in the form its anhydride, halide, ester, amide, or azide without the dehydrating substances.

Thus in reaction (a), either free acids and free amines can be used as reactants or one of the reactants i.e. the acid or amine component may be used in the form of a reactive derivative. The free amine (III) and free carboxylic acid (IV) may be reactive in the absence of dehydrating substances promoting carbamide formation provided that one uses a suitably elevated temperature of 130° to 280° C, advantageously above 150° C. Appropriately the reaction mixture is kept at elevated temperature until dehydration is substantially complete, leading to an almost quantitative yield.

When using carboxylic acid halides, the reaction is advantageously performed in the presence of an alkali metal carbonate or a tertiary amine such as pyridine or picoline, or with an e.g. equimolar excess of cyclic diamine, generally in an inert solvent such as benzene, toluene or xylene at a temperature of e.g. 15° to 50° C, advantageously up to 25° C. If necessary the reaction can be carried out at higher temperatures. The esters used as carboxylic or thiocarboxylic acid derivatives have appropriately ester groups with up to 4 C-atoms.

According to one embodiment, the diamine (III) is reacted with a halide of the acid (IV) in solution in dimethylformamide. One may thus obtain the product in the form of its hydrohalide.

A further advantage of this embodiment is the considerable purification action of the dimethylformamide. The isolation of the product can take place in conventional manner e.g. by evaporating or precipitating. Suitable precipitants wherein the reaction product is difficultly soluble or insoluble are methyl ethyl ketone, dialkyl ethers e.g. diethylether or diisopropyl ether, petroleum ether, aromatic hydrocarbons such as benzene, toluene or xylene, mono- or polyhydric alcohols with 1 to 9 C-atoms, e.g. methanol, ethanol, propanols, butanols, pentanols, hexanols, octanols, nonanols, if desired together with water; advantageously one uses acetone. These precipitants are selected depending on the chemical nature of the reagents used and/or the reaction products and other conventional solvents can also be used as precipitants provided that the reaction products are only difficultly soluble or insoluble therein.

As acid halides can in particular be used chlorides or bromides. The salts initially obtained can if desired be converted in conventional manner e.g. by double reaction into other acid addition salts.

A further advantage of this embodiment is that further portions of product can be obtained from the resulting mother liquor e.g. by evaporation and/or by adding further precipitants and/or one of the reactants.

According to a preferred embodiment of process (a), X in general formulae (I) and (IV) is oxygen, Z in formula (III) is hydrogen and $R_2$ has no amine substituents.

According to one embodiment of the process (b), one performs the reaction in an inert solvent with diphosphorus pentasulphide optionally mixed with an alkali metal sulphide, particularly potassium sulphide, to form the thioacyl compound (cf. compound 52). For example one may use as solvent toluene, xylene or pyriding; the addition of alkaline earth carbonates or oxides can increase the yield. It is also possible to use as the sulphur compound e.g. aluminium sulphide, advantageously in the presence of salts containing water of crystallisation. The compound (I) used as starting material may e.g. be made as in (a) above.

When using process (d), the reaction can e.g. take place in an inert solvent, advantageously in xylene, preferably at elevated temperature e.g. 80° to 150° C. In this embodiment it is once again advantageous to use the above-indicated alkali metal carbonates or tertiary amines or an excess of the amine to be alkylated which is about equimolecular to the quantity of amine to be reacted for the purpose of trapping the acid. It is also however possible to perform the reaction (d) at lower temperature e.g. at room temperature. This is particularly the case if the compounds (VIII) are iodides or chloromethylthiophene.

The process (e) is generally performed under elevated pressure at about 100° C to 250° C, preferably up to 160° C. As the compound (XII) advantageously benzylpiperazine - dithiocarbamic acid is used as a salt of the corresponding amine. A preferred component (XIII) is coumarillonitrile. These compounds react according to the following equation:

The reactions of type (a), particularly using a halide of the acid (IV) in dimethylformamide solution, or reacting the free acid and amine at elevated temperature and without a substance splitting off water and favoring the carbamide formation, are generally particularly easily performable technically because they take place particularly smoothly and in a very high yield. Thus no further acid-binding agent is necessary, the molar ratio of the components can be selected as 1:1, although other molar ratios e.g. 3:1 to 1:3, advantageously 1.5:1 to 1:1.5 are also possible, and any solvents present can be used again; the reagents are readily available.

For reaction (a) using carboxylic acids of formula (IV) wherein X is oxygen, dehydrating substances which aid carbamide formation are particularly carbodiimides e.g. dicyclohexylcarbodiimide, 1-cyclohex-

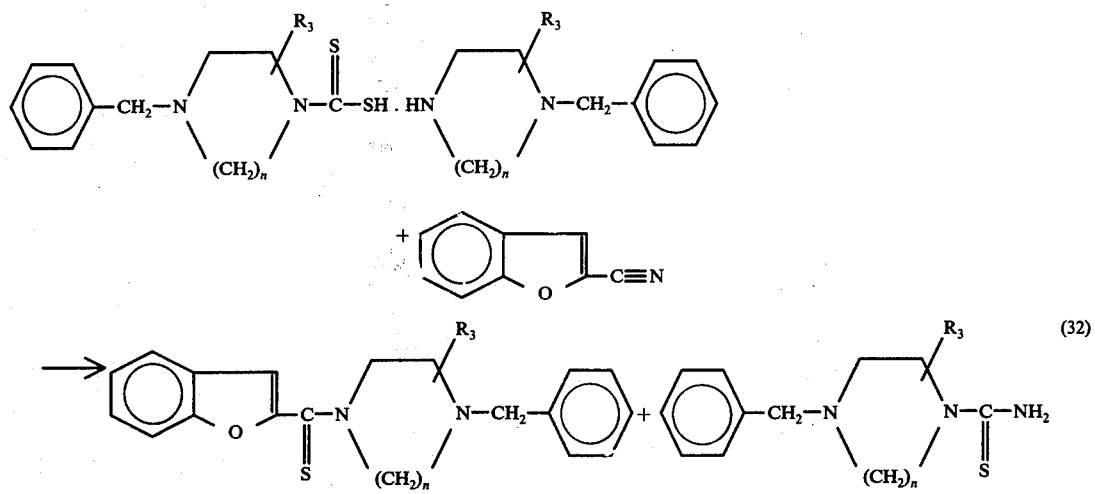

Reaction (f) is generally performed under reduced pressure whilst slowly increasing the temperature up to e.g. about 150° C, advantageously 100° C. It is also however possible to work under normal pressure. Particularly advantageous starting materials are the dithioesters of lower mercaptans particularly methyl mercaptan due to its being readily volatile. As a result, the mercaptan formed during the reaction can be removed from the reaction mixture, particularly easily:

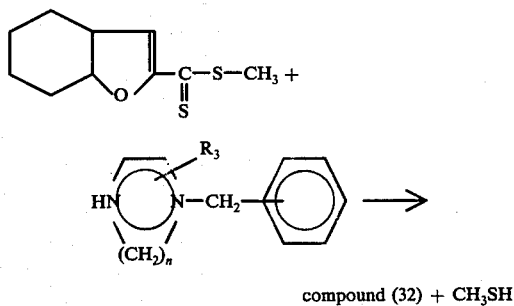

compound (32) + CH₃SH

Preferred reagents for this embodiment are methyl dithiocoumarillate and benzylpiperazine which can be reacted together with elimination of methyl mercaptan as above.

In addition to the above-indicated preferred reagents it is also possible to react other compounds of the indicated formulae.

According to the processes of the invention high yields may be obtained which can e.g. be above 95%.

yl-3-(2-morpholinomethyl)-carbodiimide, N-(3-dimethylaminopropyl)-N'-ethylcarbodiimide-hydrochloride, di-p-tolyl-carbodiimide, diisopropylcarbodiimide as well as diethylcyanamide. In addition are suitable pyrophosphites, such as bis-o-phenylene pyrophosphite, tetramethyl pyrophosphite, diethyl ethylene-pyrophosphite, and acetylenes such as ethoxyacetylene. These substances are appropriately present in the molar ratio 1:1 to 1:1.5 relative to the particular reagent i.e. the diamine or acid component. It is possible to go above or below this range but the optimum conditions exist within the range.

According to process (a), in place of the free carboxylic or thiocarboxylic acids may be used e.g. their halides or esters e.g. alkyl esters, phenyl esters or esters with N-hydroxypyridine, N-hydroxypiperidine, N-hydroxyphthalimide or N-hydroxysuccinimide. The carboxylic acid amides also suitable for process (a) can be prepared e.g. by reacting carboxylic acids and N,N'-carbonylimidazole or N,N'-carbonyl-di-s-triazine in the presence of dehydrating agents.

The cyclic diamines of formula (III) suitable for use in process (a) include for example N-benzylpiperazine or -homopiperazine, N-benzyl-N'-acylpiperazines, such as N-benzyl-N'-formylpiperazine, N-benzyl-N'-phenoxycarbonylpiperazine, N-benzyl-N'-phosphorus acid diester piperazines as well as the corresponding homopiperazine compounds.

The indicated phosphorus-containing amines can for example be obtained by reacting diethyl chlorophosphonite or ethylene chlorophosphonite and corresponding amines; the phenoxycarbonyl amines are prepared by reacting e.g. N-benzylpiperazine with bis-(2,4-dinitrophenyl)-carbonate. The above-indicated phosphorus-containing amines are represented by two compounds (X) and (XI):

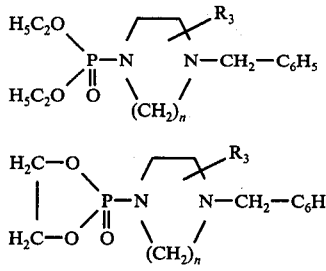

An advantage of process (d) is the relatively favourable storage stability of the piperazides.

It is also possible to aid dehydration by entraining with an inert gas which does not participate in the reaction e.g. nitrogen, hydrogen, or other inert gas.

With the aid of thin layer chromatography it is possible to follow the production of product and the synthesis can be concluded at optimum yield. The $R_f$-values obtained also serve to characterise and define the new diamines; the $R_f$-value should be understood to mean the value which is obtained by dividing the distance between the starting point of the substance and the spot centre by the distance between the starting line and the solvent front.

The isolation of the products prepared according to the invention can for example take place by distillation and/or crystallisation.

Suitable cyclic diamines according to formula (III) include for example:

(i) aralkylpiperazines or aralkylhomopiperazines such as benzylpiperazine, phenylethylpiperazine, (2-phenylethyl) piperazine, (2-phenylpropyl)piperazine, tetrahydronaphthylmethylpiperazine, indanylmethylpiperazine, diphenylmethylpiperazine, naphthylmethylpiperazine as well as the corresponding homopiperazine compounds;

(ii) cycloalkyl-alkylpiperazines such as cyclopentylmethylpiperazine, cyclohexylmethylpiperazine, cyclopentylethylpiperazine, cyclohexylethylpiperazine as well as the corresponding homopiperazine compounds;

(iii) heteroalkylpiperazines or homopiperazines such a furfurylpiperazine, tetrahydrofurfurylpiperazine, thenylpiperazine, pyridylmethylpiperazine, quinolylmethylpiperazine, isoquinolylmethylpiperazine, piperidylmethylpiperazine, as well as the corresponding homopiperazine compounds;

(iv) hydroxylated derivatives or derivatives of the above-indicated compounds which are halogenated, nitrated, alkylated or alkoxylated in the aromatic nucleus.

Suitable carboxylic or thiocarboxylic acids of formula (IV) include for example furan carboxylic acid, dihydrofuran carboxylic acid, tetrahydrofuran carboxylic acid, pyran-, dihydropyran- and tetrahydropyran-carboxylic acids, coumarillic acid, dihydrocoumarillic acid, thiophene carboxylic acid, dihydrothiophene carboxylic acid, pyrrole carboxylic acid, dihydropyrrole carboxylic acid, pyrrolidine carboxylic acid, pyridine carboxylic acid, piperidine carboxylic acid, dihydropyridine carboxylic acid and the corresponding thiocarboxylic acids of the above-indicated compounds; chromen-(3)-ylcarboxylic acids and 5-bromocoumarillic acid; also derivatives of any of the above-indicated acids having the substituents described under $R_1$.

In place of the acids it is possible in each case to use for process (a) the corresponding acid halide, advantageously the bromide or chloride, or the corresponding alkyl esters e.g. of alcohols with 1 to 4 C-atoms e.g. methyl or ethyl esters.

For process (c) one can e.g. use as amine moieties of the amino magnesium halide the above-mentioned piperazines or homopiperazines. As cyclic amino magnesium halides of general formula (V) bromides and chlorides are particularly suitable. This reaction generally takes place in an ethereal solution from which subsequently the desired compound is liberated in the conventional manner. Suitable nitriles of general formula (VI) are for example the nitriles of the above-indicated acids.

If monoacylamines of formula (VII) are reacted according to the process (d) then one may start for example with the piperazides or homopiperazides of the above-indicated carboxylic or thiocarboxylic acids.

For example, the compound N-benzylcoumarillic acid piperazide can be prepared according to various processes. According to process (a), for example, coumarillic acid and benzylpiperazine are reacted in the presence of dicyclohexylcarbodiimide. In place of the acid it is also possible to use the corresponding chloride or methyl ester. According to process (d) coumarillic acid piperazide is reacted with benzyl chloride.

Compounds according to the invention include those according to formulae 1 to 58 in Table 2 hereinafter. The characteristics of the compounds according to the invention were determined in various ways, namely by melting point, thin layer chromatography, and ultra-violet and infra-red spectroscopy. The melting points are also shown in Table 2.

The compounds according to the invention have interesting therapeutic properties. They can for example be used as psychotherapeutic medicaments, being relatively free from the undesirable side effects which considerably restricts the therapeutic application of other medicaments. Certain of the compounds effective as antidepressants exhibit in therapeutically interesting doses neither sedation nor central stimulation. The sympathetic nervous system is substantially not influenced by these compounds. No effects detrimental to the heart have been observed. In this, these compounds differ advantageously from comparable known antidepressant substances. In addition, certain compounds also have analgesic, anti-inflammatory, anti-spasmodic, vasodilatory and antipyretic activities. In addition the compounds have a good physiological acceptability due to their low toxicity. The stability of the compounds, mainly obtained in crystalline form, permits the preparation of medicament compositions for e.g. oral, parenteral or rectal administration.

These compositions can be made by conventional procedures, e.g. by mixing the active ingredient with suitable and compatible adjuvants such as starch, lactose, cellulose derivatives, stearic acid or salts thereof, solvents, solubilisers, suppository bases, chlorides, phosphates and carbonates e.g. sodium bicarbonate, and forming for example in known manner powders, tablets, dragees, capsules, suppositories, solutions or suspensions.

Comparative Tests

The therapeutic activity of compounds according to the invention was determined by measurement of reserpine antagonism (B. Rubin et al., "J. Pharmacol. exp. Therap." Vol 120 (1957) p 125) and by the effect on the fighting behaviour of fighting mice in the test arrangement of G. Y. Yen et al., (Arch. Int. Pharmacodyn, Vol 123 (1959) p 179).

The values obtained during the reserpine test are given in the following Table 1:

TABLE 1

| Compound No. | % Influence on reserpine ptosis 1 hr after 25 mg/kg of substance orally | $LD_{50}$ mg/kg i.p. mouse |
|---|---|---|
| 1 | −50 | 320 (2050 orally) |
| 3 | −22 | 1000–1500 |
| 5 | −50 | 100–250 |
| 16 | −54 | 100–250 (1980 orally) |
| 20 | −32 | 100–150 |
| 22 | −23 | 250–500 |
| 42 | −49 | 100–250 |
| 5-(3′-dimethyl-aminopropyl)-10-11-dihydro-5-H-dibenz-[b,f]-azepine hydrochloride (Comparison substance) | −76 | 130 (380 orally) |

From the above Table it can be seen that the compounds according to the invention have a more favourable $LD_{50}$ than the comparative substance, which has a high activity but also a high toxicity.

The compounds according to the invention were also tested for their influence on coronary through-flow on the heart mechanogram and for their spasmolytic action.

The latter test was performed on the isolated guinea pig intestine by the method of R. Magnus ("Pflugers Archiv" Vol 102 (1904) p 123). The spasmolytic action was determined against acetylcholine in a dose of $10^{-7}$ g/ml, $10^{-7}$ g/ml of histamine and $10^{-4}$ mg/ml of barium chloride, and the effective dose ($ED_{50}$) established in μg/ml. The results are given in Table 1a. For comparison the activities of the commercially available product imipramine as shown.

TABLE 1a

| Compound No. | Dose in 82 g | Coronary through-flow Change (%) | Duration (min) | Action on the heart mechanogram | Spasmolytic action against: Acetylcholine | Histamine | $BaCl_2$ |
|---|---|---|---|---|---|---|---|
| | | | | | ($ED_{50}$ in μg/ml) | | |
| Comparison compound | | | | | | | |
| Imipramine | 10 | +19/−18 | 0.5/21 | — | 0.01–0.1 | 0.001 | 0.1–1.0 |
| | 20 | +28/−29 | 0.6/26 | — | | | |
| | 30 | +84/−22 | −/>10 | — | | | |
| Compounds according to the invention | | | | | | | |
| 1 | 10 | + | 0.5 | φ | 10 | 1–10 | 1–10 |
| | 30 | +38 | 1.0 | φ | | | |
| | 100 | +120 | 26.0 | — | | | |
| 2 | | | | | > | 1–10 | 1–10 |
| 16 | | | | | φ | φ | φ |
| 17 | 10 | +8 | 1.0 | φ | | | |
| | 30 | +25 | 1.0 | φ | | | |
| 20 | 10 | +25 | | | 3 | 1 | 0.3 |
| | 50 | +50 | | | | | |
| 21 | | | | | φ | 0.1 | φ |
| 24 | | | | | φ | φ | φ |
| 25 | 6 | +18 | 8.0 | (—) | 1–10 | 1–10 | >10 |
| | 30 | +31 | 27.0 | | | | |
| 26 | 30 | +13 | 5 | | | | |
| | 100 | +21 | >12 | | | | |
| 28 | | | | | φ | φ | φ |
| 29 | | | | | >10 | >10 | >10 |
| 30 | 10 | +90 | 12 | | | | |

(—) = reduction of 10%
— = reduction of 25%
——— = reduction of 50%
φ = substantially no action As can be seen from the above Table, the comparison compound exhibits initially a brief rise in coronary flow but this changes into a long contraction, and thus damages the heart. As opposed to this, the compounds according to the invention dilate and do not contract the coronary vessels.

In connection with the action on the heart mechanogram the comparison compound at a dose of 10 or 20 μg exhibits a reduction of the heart muscle force of 25% and at a dose of 30 μg a reduction of 50%. The compounds according to the invention have substantially no action during this test with the exception of compound 1 which, at a dose of 100 μg, exhibits a 25% reduction. However this is not linked with damage as is the case with the comparison compound because at this dose there is simultaneously a considerable increase in the coronary through-flow without subsequent contraction of the vessel. Compound 25 has a slight action of less than 25% at a dose of 30 μg.

The spasmolytic action of the substances according to the invention is also relatively small.

From Table 1a it can be seen that the peripheral sympathetic nervous system is substantially not influenced by the anti-depressant compounds according to the invention.

In therapeutic doses they cause neither stimulation nor sedation. In addition they inhibit the aggressiveness of fighting mice. Despite the good anti-depressant properties, we have not observed undesirable side effects such as anti-cholinergic, anti-histame, sympatholytic, sympathomimetic or anti-serotonic effects.

From the activities of the known tricyclic compounds it could not be expected that the compounds according to the invention, in addition to reserpine antagonism i.e. an anti-depressant action with simultaneous tranquillising action, would have only a slight or no influence on the peripheral sympathetic nervous system as well as substantially no unfavourable action on the heart and circulatory system. They have therefore a new spectrum of activity and also a more favourable toxicity than the comparison compounds.

In order that the invention may be better understood, the following Examples are given by way of illustration. The figures after each title refer to Table 2.

EXAMPLE 1

N-(2,4,6-Trimethylbenzyl)-N-2-methyl-5,6-dihydro-pyran-3-carbonyl-piperazine-hydrochloride (No. 26)

A solution of 43.6 g of 2,4,6-trimethylbenzylpiperazine (0.2 mol) in 250 ml of xylene is mixed with 30.4 g of finely pulverised anhydrous potassium carbonate (0.22 mol). Accompanied by vigorous stirring, 32.1 g of 2-methyl-5,6-dihydro-pyran-3-carbonyl chloride (0.2 mol; boiling point 106° C (10 mm Hg) in 200 ml of xylene are added over 5 minutes at room temperature. The reaction mixture is refluxed for 3 hours. After cooling to room temperature the solution is suction filtered from the solid product and the filtrate is evaporated in vacuo. The residue is taken up in 300 ml of methanol and mixed with ethereal hydrochloric acid. The precipitate obtained is washed with acetone and ether. The yield of the title compound is 68.0 g (89.8%). For further purification the substance is recrystallised from isopropanol. The physical data of the new compound are given in Table 3 under number 26.

In the same way can be prepared the compounds N-benzyl-coumarillic acid piperazide (No. 1), N-(tetrahydrofuryl-2-methyl)-coumarillic acid piperazide (No. 15) and N-benzylthiophene-2-carboxylic acid piperazide (No. 31) and their hydrochlorides, as well as compounds Nos. 37 to 43 in Table 2.

EXAMPLE 2

N-Benzyl-coumarillic acid piperazide (No. 1)

A solution of 902.5 g (5 mol) of freshly distilled coumarillyl chloride (boiling point 138° C/12mm Hg) in 2 liters of benzene is added to a solution of 1760 g of N-benzylpiperazine (10 mol in 10 liters of benzene) in a jet accompanied by vigorous stirring, producing as far as possible a homogeneous mixture before precipitation occurs. A thick precipitate is rapidly formed which solidifies the reaction mixture. Frequent stirring and agitation takes place over a period of about 2 hours. After cooling to room temperature, the solid product is filtered on a suction filter, washed with benzene and then with acetone. The solid product is N-benzylpiperazine hydrochloride from which the base can be recovered. The filtrate (benzene-acetone solution) is evaporated in vacuo and the residue is distilled under high vacuum. After a small first fraction of N-benzylpiperazine, the desired N-benzylcoumarillic acid piperazide distills at 220° to 270° C/0.1 Torr and immediately solidifies in crystalline form.

Yield: 1445 g (90% of theory); sometimes the yield can reach 95%.

If an alcoholic solution of the product is strongly acidified with alcoholic hydrochloric acid a colourless precipitate is precipitated. After cooling to room temperature the precipitate is filtered on a suction filter and washed with acetone. The N-benzyl-coumarillic acid piperazide hydrochloride can be purified by recrystallisation from methanol or from dimethylformide - acetone, or by vacuum sublimation. The product obtained has particularly advantageous properties.

Yield: 1600 g (almost quantitative)

M.p.: 238° C accompanied by decomposition (sublimation from about 170° C)

In the same way the acid addition salts with other mono- or polybasic acids can be prepared; using polybasic acids, generally acid salts are formed.

Compounds 2 to 14, 16 to 25 and 27 to 29 can be prepared by the general method of the present Example.

Using the general method of Example 2 the following diamines and their salts listed in Table 2 were obtained:

No. 2. N-(4-chloro)-benzyl-coumarillic acid piperazide as well as its hydrochloride No. 3. N-(3,4-dichlorobenzyl)-coumarillic acid piperazide as well as its hydrochloride No. 4. N-(2,4-dichlorobenzyl)-coumarillic acid piperazide as well as its hydrochloride No. 5. N-(4-fluorobenzyl)-coumarillic acid piperazide as well as its hydrochloride No. 6. N-(4-bromobenzyl)-coumarillic acid piperazide as well as its hydrochloride No. 7. N-(4-methylbenzyl)-coumarillic acid piperazide as well as its hydrochloride No. 8. N-(2,4,6-trimethylbenzyl)-coumarillic acid piperazide as well as its hydrochloride No. 9. N-(4-methoxybenzyl)-coumarillic acid piperazide as well as its hydrochloride No. 10. N-(3,4,5-trimethoxybenzyl)-coumarillic acid piperazide as well as its hydrochloride No. 11. N-(4-hydroxybenzyl)-coumarillic acid piperazide as well as its hydrochloride No. 12. N-(4-nitrobenzyl)-coumarillic acid piperazide as well as its hydrochloride No. 13. N-diphenylmethyl-coumarillic acid piperazide as well as its hydrochloride No. 14. N-phenylethyl-coumarillic acid piperazide as well as its hydrochloride No. 16. N-thenyl-coumarillic acid piperazide as well as its hydrochloride No. 17. N-benzyl-coumarillic acid homopiperazide as well as its hydrochloride No. 18. N-cyclohexylmethyl-coumarillic acid piperazide as well as its hydrochloride No. 19. N-pyridyl-3-methyl-coumarillic acid piperazide as well as its hydrochloride No. 20. N-benzyl-2,3-dihydrocoumarillic acid piperazide as well as its hydrochloride No. 21. N-benzyl-furan-2-carboxylic acid piperazide as well as its hydrochloride No. 22. N-3,4-dichlorobenzyl-furan-2-carboxylic acid piperazide as well as its hydrochloride No. 23. N-2,4-dichlorobenzyl-furan-2-carboxylic acid piperazide as well as its hydrochloride No. 24. N-benzyl-[6-methyl-2,3-dihydropyran-5-carboxylic acid]piperazide as well as its hydrochloride No. 25. N-3,4-dichlorobenzyl-[6-methyl-2,3-dihydropyran-5-carboxylic acid]-piperazide as well as its hydrochloride No. 27. N-4-nitrobenzyl-[6-methyl-2,3-dihydropyran-5-carboxylic acid]-piperazide as well as its hydrochloride No. 28. N-thenyl-[6-methyl-2,3-dihydropyran-5-carboxylic acid piperazide as well as its hydrochloride No. 29. N-benzyl-[6-methyl-tetrahydropyran-5-carboxylic acid]-piperazide as well as its hydrochloride

DETERMINATION OF PHYSICAL CONSTANTS FOR THE PRODUCTS

The structure and composition of the cyclic diamines according to the invention was determined by elementary analysis and UV, IR, and NMR and mass spectroscopy.

To characterise the products obtained (see Table 2) they were examined by thin layer chromatography. The results are given in Table 3. The chromatographic system was as follows:

| Absorbent | : | Silica gel $F_{254}$ (coated plates supplied by Merck, Darmstadt) |
|---|---|---|
| Plate size | : | 20 × 20 cm |
| Solvent | : | I a. Chloroform-methanol-formic acid 96 : 3 : 1 (chamber saturation) |
| | | I b. Chloroform-methanol-formic acid 96 : 3 : 1 (without chamber saturation) |
| | | II. Chloroform (without chamber saturation) |
| | | III. Ethylacetate-hexane 80 : 20 (without chamber saturation) |
| | | IV. Chloroform-methanol-formic acid 80 : 15 : 5 (without chamber saturation) |
| Running distance | : | 15 cm |

The results of UV and IR spectroscopy are shown in Table 3.

EXAMPLE 3

N-Benzyl-coumarillic acid piperazide (No. 1; cf. also Example 2)

A solution of 18.0 g of coumarillyl chloride (0.1 mol) in 180 ml of pyridine is mixed with a solution of 17.6 g (0.1 mol) of N-benzylpiperazine in 70 mol of pyridine. The mixture is refluxed for 30 minutes. After cooling to room temperature the precipitate, which is a pyridine adduct, is separated and boiled with 200 ml of water.

After cooling, the solid N-benzyl-coumarillic acid piperazide is isolated and taken up in methylene chloride. The solution is then extracted twice with water and subsequently dried with sodium sulphate. After removing the methylene chloride by triturating with ether 26 g of N-benzyl-coumarillic acid piperazide (m.p. 85° C) are obtained. From the pyridine mother liquor a further portion of the desired end product can be isolated. The yield exceeds 85% of theory.

EXAMPLE 4

N-Benzyl-indole-2-carboxylic acid piperazide (No. 30)

18.9 g (0.1 mol) of ethyl indole-2-carboxylate and 17.6 g (0.1 mol) of N-benzylpiperazine are refluxed in 100 ml of xylene until thin layer chromatographic examination shows complete reaction.

To work up the mixture, the xylene is evaporated in vacuo and the residue taken up in a little ether. After adding about 100 ml of petroleum ether a certain amount of solid product is separated. The remaining solution is evaporated. The residue which remains is crystallised from ether. The desired title compound is obtained in the form of colourless needles, m.p. 150° C.

EXAMPLE 5

N-Benzyl-indole-2-carboxylic acid piperazide (No. 30; cf. also Example 4)

24.14 g of indole-2-carboxylic acid (0.15 mol) and 26.4 g of N-benzylpiperazine (0.15 mol) are heated until a clear solution is obtained in 300 ml of xylene. After cooling to room temperature, a solution of 30.9 g of dicyclohexylcarbodiimide (0.15 mol) is added and refluxing takes place for 1 hour. After cooling a solid product separates; the xylene solution is evaporated and the residue recrystallised several times from ether. Colourless needles of the title compound (m.p. 150° C) are obtained. In the same way compound No. 1 may also be prepared.

EXAMPLE 6

N-Benzyl-coumarillic acid piperazide-hydrochloride (No. 1; cf. also Example 2)

2.3 g of coumarillic acid piperazide (0.01 mol) are suspended in 10 ml of xylene and mixed with a solution of 0.6 g of benzyl chloride (0.005 mol) in 5 ml of xylene. The mixture is kept for 1 hour at boiling point, cooled, the coumarillic acid piperazide hydrochloride is separated and the filtrate mixed with ethereal hydrochloric acid. The precipitate obtained is isolated and recrystallised from methanol or water. (m.p. 238° C accompanied by decomposition; yield: above 95%).

The isolated coumarillic acid piperazide hydrochloride can after liberating the base be used in further mixtures.

EXAMPLE 7

N-Benzyl-thiocoumarillic acid piperazide hydrochloride (No. 32)

32.0 g of N-benzyl-coumarillic acid piperazide (0.1 mol) are refluxed in 300 ml of toluene and mixed portionwise with 11.5 g of diphosphorous pentasulphide (0.052 mol). Refluxing takes place for 1.5 hours and subsequently the reaction solution is decanterd from the small amount of undissolved resinous by-products. After evaporating, the residue is taken up in ether.

The solution of the base is purified by filtration and mixed with ethereal hydrochloric acid solution. The title compound, after recrystallising from ethanol, has a melting point of 204° C to 205° C.

Analogously are obtained:

N-benzyl-furan-2-thiocarboxylic acid piperazide (No. 33);
N-benzyl-N'-[6-methyl-2,3-dihydropyran-5-thiocarbonyl]piperazine (No. 34);
N-3,4-dichlorobenzyl-N'-[6-methyl-2,3-dihydropyran-5-thiocarbonyl]-piperazine (No. 35) as well as the hydrochlorides of these compounds.

EXAMPLE 8

N-Benzyl-N'-benzofuran-2-carbimido-piperazine-dihydrochloride (No. 36)

4.9 g of magnesium filings (0.2 gram atoms) are covered with 50 ml of ether and accompanied by stirring, a solution of 21.8 g of ethyl bromide (0.2 mol) in 20 ml of ether is added dropwise over 20 minutes. The reaction mixture is then boiled for 30 minutes. Subsequently a solution of 35.2 g of N-benzylpiperazine (0.2 mol) in 200 ml of ether is added dropwise over 20 minutes. After further dropwise addition of a solution of 28.6 g of coumarillonitrile (melting point 33° to 34° C; 0.2 mol) in 400 ml of benzene the now clear solution is refluxed for 1 hour.

After cooling, an aqueous solution of 2 mol of ammonium chloride is added accompanied by stirring and the organic phase separated and dried. After evaporating, the title compound is transformed into the hydrochloride. The product crystallises from acetone/water with 1.5 mols of water of crystallisation.

M.p. 253° C accompanied by decomposition (m.p of the base 150° C)

Yield: 14.8 g (38% of theory).

From the mother liquor a further portion of the desired product is obtained.

EXAMPLE 9

N-Benzyl-coumarillic acid piperazide (No. 1)

A solution of 17.6 g (0.1 mol) of N-benzylpiperazine in 40 ml of dimethylformamide is mixed, with vigorous stirring, with a solution of 18.1 g of coumarillyl chloride (0.1 mol) in 30 ml of dimethylformamide. After exothermic reaction a white precipitate is obtained from the initially homogeneous solution which on boiling under reflux again passes into solution. The pale brown reaction mixture is boiled for 1 hour and whilst still hot poured with stirring into 150 ml of acetone. The desired product is precipitated from the initially homogeneous solution. After cooling, the mixture is acidified with 3 ml of concentrated hydrochloric acid. The precipitate is suction filtered, washed with acetone and dried. The product is obtained with a particularly high purity.

Yield: 33.5 g of colour product (94% of theory)

The product can be recrystallised from water or methanol. M.p. 238° to 243° C accompanied by decomposition.

After evaporating the original dimethylformamide mother liquor a further small portion of product can be isolated.

If in place of the N-benzylpiperazine an equimolar quantity of 20.4 g (0.1 mol) of N-(2-phenylpropyl)-piperazine is reacted, then N-(2-phenylpropyl)-coumarillic acid piperazide hydrochloride is obtained in the same good yield.

EXAMPLE 10

N-Benzylthiocoumarillic acid piperazide hydrochloride 20.8 g of methyl dithiocoumarillate (0.1 mol) and 17.6 g of N-benzylpiperazine (0.1 mol) are well mixed and heated on a boiling water bath; methyl mercaptan is eliminated. The temperature is raised to 150° C until complete reaction takes place and the remaining methyl mercaptan is removed in vacuo. After conversion into the hydrochloride according to Example 1, the product obtained is recrystallised from ethanol. A substance with a melting point of 205° to 207° C is obtained.

EXAMPLE 11

N-Benzyl-thiocoumarillic acid piperazide hydrochloride 42.9 g of N-benzylpiperazinium N-benzylpiperazone-N'-dithiocarbamate (0.1 mol) and 14.3 g of coumarillonitrile are heated in the autoclave for about 8 hours to 150° C. After conversion to the hydrochloride as in Example 1 the title product obtained is fractionally recrystallized from ethanol. (Melting point 205° to 207° C).

EXAMPLE 12

N-Benzyl-coumarillic acid piperazide (No. 1)

A mixture of 48.6 g of coumarillic acid (0.3 mol) and 52.8 g of N-benzylpiperazine (0.3 mol) is heated to 250° C; complete melting takes place at about 170° C. At about 210° C elimination of water commences. The reaction mixture is kept at 250° C until the desired quantity of water (0.3 mol) is eliminated. The reaction product is distilled at 0.2 mm Hg. After a small first fraction the main fraction collected from 215° C is obtained in the form of a viscous light yellow oil which immediately solidifies in crystalline form. (Melting point 85° C, yield 95%).

Using the same general method as the above Example, compounds 44 to 51 and 53 to 58 (Table 2a) as well as the already described compound 42 were obtained from the starting materials illustrated in Tables 4 and 5.

EXAMPLE 13

N-Thenyl-N'-thiophen-2-thiocarbonyl-piperazine-hydrochloride (No. 52)

Into a solution of 32.9 g of N-thenyl-N'-thiophen-2-carbonyl-piperazine (0.1 mol) in 300 ml of toluene are introduced at boiling temperature in the course of one hour 11.5 g of diphosphorus pentasulphide (0.052 mol). Boiling continues for a further 2 hours followed by hot filtration. The solvent is removed in vacuo. After adding ethereal hydrochloric acid to the clear ethereal extract of the residue, 21g (60% yield) of the desired title product are obtained. After recrystallizing from ethanol, the yellow product obtained decomposes at 236° C.

It is not intended that the examples given herein should be construed to limit the invention thereto, but rather they are submitted to illustrate some of the specific embodiments of the invention. Resort may be had to various modifications of the invention. Resort may be had to various modifications and variations of the present invention without departing from the spirit of the discovery or the scope of the appended claims.

TABLE 2

| Compound No. | Coumarillic acid derivative | M.p. | Rf-values Ia | Ib | II | III | IV | Example |
|---|---|---|---|---|---|---|---|---|
| 1 | [structure: benzofuran-C(=O)-N-piperazine-N-CH₂-phenyl · HCl] | 238° Z⁺⁾ | 0.11 | 0.28 | 0.19 | 0.58 | | 1,2,3,4,5 |
| 2 | [structure: benzofuran-C(=O)-N-piperazine-N-CH₂-phenyl-Cl · HCl] | 230° Z | 0.19 | 0.48 | 0.21 | 0.56 | | 2 |

TABLE 2-continued

| # | Structure | mp | | | | | | |
|---|---|---|---|---|---|---|---|---|
| 3 | benzofuran-2-C(O)-N(piperazine)N-CH₂-C₆H₃(Cl)(Cl) · HCl | 211° Z | 0.35 | 0.59 | 0.25 | 0.58 | | 2 |
| 4 | benzofuran-2-C(O)-N(piperazine)N-CH₂-C₆H₃(Cl)(Cl) · HCl | 235° Z | 0.41 | 0.73 | 0.35 | 0.76 | | 2 |
| 5 | benzofuran-2-C(O)-N(piperazine)N-CH₂-C₆H₄-F · HCl | 250° Z | 0.13 | 0.36 | 0.19 | 0.49 | | 2 |
| 6 | benzofuran-2-C(O)-N(piperazine)N-CH₂-C₆H₄-Br · HCl | 232° Z | 0.21 | 0.45 | 0.21 | 0.53 | | 2 |
| 7 | benzofuran-2-C(O)-N(piperazine)N-CH₂-C₆H₄-CH₃ · HCl | 219° | 0.11 | 0.25 | 0.19 | 0.47 | | 2 |
| 8 | benzofuran-2-C(O)-N(piperazine)N-CH₂-C₆H₂(CH₃)₃ · HCl | 250° Z | 0.33 | 0.79 | 0.63 | 0.86 | | 2 |
| 9 | benzofuran-2-C(O)-N(piperazine)N-CH₂-C₆H₄-O-CH₃ · HCl | 224° Z | 0.10 | 0.25 | 0.13 | 0.39 | | 2 |
| 10 | benzofuran-2-C(O)-N(piperazine)N-CH₂-C₆H₂(OCH₃)₃ · HCl | 280° Z | 0.09 | 0.30 | 0.09 | 0.20 | | 2 |
| 11 | benzofuran-2-C(O)-N(piperazine)N-CH₂-C₆H₄-OH · HCl · H₂O | 248° Z | 0.03 | 0.03 | 0.08 | 0.34 | | 2 |
| 12 | benzofuran-2-C(O)-N(piperazine)N-CH₂-C₆H₄-HO₂ · HCl | 231–233 | 0.36 | 0.69 | 0.31 | 0.51 | | 2 |
| 13 | benzofuran-2-C(O)-N(piperazine)N-CH(C₆H₅)₂ · HCl | 208–210 | 0.58 | 0.84 | 0.64 | 0.87 | | 2 |
| 14 | benzofuran-2-C(O)-N(piperazine)N-CH₂-CH₂-C₆H₅ · HCl | 243 Z | 0.11 | 0.30 | 0.14 | 0.32 | | 2 |
| 15 | benzofuran-2-C(O)-N(piperazine)N-CH₂-(tetrahydrofuran) · HCl | 197 Z | 0.05 | 0.12 | 0.07 | 0.07 | | 1 |
| 16 | benzofuran-2-C(O)-N(piperazine)N-CH₂-(thiophene) · HCl | 255 Z | 0.20 | 0.49 | 0.26 | 0.63 | | 2 |
| 17 | benzofuran-2-C(O)-N(piperazine)N-CH₂-C₆H₅ · HCl | 135 | 0.06 | 0.15 | 0.10 | 0.28 | | 2 |
| 18 | benzofuran-2-C(O)-N(piperazine)N-CH₂-(cyclohexyl) · HCl | 257 Z | 0.11 | 0.25 | 0.21 | 0.69 | | 2 |

TABLE 2-continued

| No. | Structure | M.P. °C | Rf Ia | Rf Ib | II | III | IV | Example |
|---|---|---|---|---|---|---|---|---|
| 19 | benzofuran-2-carbonyl-piperazine-CH₂-(3-pyridyl) · HCl | 245 Z | 0.04 | 0.08 | 0.01 | 0.03 | | 2 |
| 20 | 2,3-dihydrobenzofuran-2-carbonyl-piperazine-CH₂-phenyl · HCl | 220–221 | 0.35 | 0.64 | 0.18 | 0.39 | | 2 |

| No. | Furan carboxylic acid derivative | M.P.° C | Ia | Ib | II | III | IV | Example |
|---|---|---|---|---|---|---|---|---|
| 21 | furan-2-carbonyl-piperazine-CH₂-phenyl · HCl | 237 Z | 0.07 | 0.17 | 0.19 | 0.39 | | 2 |
| 22 | furan-2-carbonyl-piperazine-CH₂-(3,4-dichlorophenyl) · HCl | 143 Z | 0.35 | 0.64 | 0.29 | 0.63 | | 2 |
| 23 | furan-2-carbonyl-piperazine-CH₂-(2,4-dichlorophenyl) · HCl | 240 Z | 0.30 | 0.47 | 0.32 | 0.65 | | 2 |

Pyran carboxylic acid derivatives

| No. | Structure | M.P. | Ia | Ib | II | III | IV | Example |
|---|---|---|---|---|---|---|---|---|
| 24 | 2-methyl-3,4-dihydro-2H-pyran-3-carbonyl-piperazine-CH₂-phenyl · HCl | 233 | 0.07 | 0.31 | 0.10 | 0.17 | | 2 |
| 25 | 2-methyl-3,4-dihydro-2H-pyran-3-carbonyl-piperazine-CH₂-(3,4-dichlorophenyl) · HCl | 105–107 | 0.21 | 0.36 | 0.17 | 0.17 | | 2 |
| 26 | 2-methyl-3,4-dihydro-2H-pyran-3-carbonyl-piperazine-CH₂-(2,4,6-trimethylphenyl) · HCl · ½ H₂O | 238 Z | 0.22 | 0.39 | 0.21 | 0.54 | | 1 |
| 27 | 2-methyl-3,4-dihydro-2H-pyran-3-carbonyl-piperazine-CH₂-(4-nitrophenyl) · HCl · H₂O | 204–205 | 0.23 | 0.37 | 0.18 | 0.13 | | 2 |
| 28 | 2-methyl-3,4-dihydro-2H-pyran-3-carbonyl-piperazine-CH₂-(2-thienyl) · HCl | 209–210 | 0.13 | 0.21 | 0.13 | 0.17 | | 2 |
| 29 | 2-methyltetrahydropyran-3-carbonyl-piperazine-CH₂-phenyl · HCl | 250–252 | 0.05 | 0.08 | 0.05 | 0.10 | | 2 |

| No. | Indole carboxylic acid derivatives | M.p. | Ia | Ib | II | III | IV | Example |
|---|---|---|---|---|---|---|---|---|
| 30 | indole-2-carbonyl-piperazine-CH₂-phenyl | 150° | 0.07 | 0.14 | 0.10 | 0.41 | | 4,5 |

Thiophenbarboxylic acid derivatives

| No. | Structure | M.p. | Ia | Ib | II | III | IV | Example |
|---|---|---|---|---|---|---|---|---|
| 31 | thiophene-2-carbonyl-piperazine-CH₂-phenyl · HCl | 237° Z | 0.09 | 0.27 | 0.14 | — | | 1 |

Thiocarboxylic acid amide

TABLE 2-continued

| No. | Structure | M.P. | Ia | Ib | II | III | IV | Example |
|---|---|---|---|---|---|---|---|---|
| 32 | benzofuran-2-C(O)-N(piperazine)N-CH₂-phenyl · HCl | 204–05° | 0.43 | 0.73 | 0.51 | 0.86 | | 7 |
| 33 | furan-2-C(O)-N(piperazine)N-CH₂-phenyl · HCl | 211–12° | 0.29 | 0.57 | 0.51 | 0.84 | | 7 |
| 34 | dihydropyran-CH₃-C(S)-N(piperazine)N-CH₂-phenyl · HCl | 216–17° | 0.31 | 0.55 | 0.40 | 0.77 | | 7 |
| 35 | dihydropyran-CH₃-C(O)-N(piperazine)N-CH₂-(3,4-dichlorophenyl) · HCl | 201–02° | 0.55 | 0.79 | 0.55 | 0.80 | | 7 |

Amidine

| 36 | benzofuran-2-C(=NH)-N(piperazine)N-CH₂-phenyl · 2 HCl | 253° | — | — | — | — | 0.52 | 8 |

|  |  |  | \multicolumn{5}{c}{Rf-values} |  |
| No. | Coumarillic acid derivatives | M.P. | Ia | Ib | II | III | IV | Example |
|---|---|---|---|---|---|---|---|---|
| 37 | benzofuran-2-C(O)-N(piperazine)N-CH₂-quinoline · HCl | 207° | 0.15 | 0.43 | 0.08 | 0.17 | 0.83 | 1 |
| 38 | benzofuran-2-C(O)-N(piperazine)N-CH₂-indane · HCl | 220° | 0.14 | 0.37 | 0.17 | 0.54 | 0.83 | 1 |
| 39 | benzofuran-2-C(O)-N(piperazine)N-CH₂-(3-CF₃-phenyl) · HCl | 220° | 0.34 | 0.71 | 0.24 | 0.63 | 0.88 | 1 |
| 40 | benzofuran-2-C(O)-N(piperazine)N-CH₂-(5-Cl-thiophene) · HCl | 235° | 0.37 | 0.76 | 0.26 | 0.65 | 0.90 | 1 |
| 41 | furan-2-C(O)-N(piperazine)N-CH₂-thiophene · HCl | 227° | 0.12 | 0.21 | 0.13 | 0.41 | — | 1 |
| 42 | thiophene-2-C(O)-N(piperazine)N-CH₂-thiophene · HCl | 240° | 0.15 | 0.25 | 0.15 | 0.51 | — | 1 |
| 43 | benzofuran-2-C(O)-N(piperazine)N-CH₂-CH(CH₃)-phenyl · HCl | | | | | | | | |

N-(2-phenylpropyl)-coumarillic acid piperizide hydrochloride

+) Z = accompanied by decomposition

TABLE 2a

| | Structure | Melting point |
|---|---|---|
| 44 | isonicotinoyl-N(piperazine)N-CH₂-phenyl | 83° |
| 45 | nicotinoyl-N(piperazine)N-CH₂-phenyl | 111° |

TABLE 2a-continued

| # | Structure | Melting point |
|---|---|---|
| 46 | pyridine-2-C(O)-piperazine-N-CH₂-phenyl; a) Base, b) Base · 1,5 H₂O, c) HCl | a) 195–200°/0,4 mmHg; b) 75°; c) 235° |
| 47 | thiophene-2-C(O)-piperazine-N-CH₂-CH(CH₃)-phenyl · HCl | 245° |
| 48 | thiophene-2-C(O)-piperazine-N-CH₂-(5-Cl-thiophen-2-yl) · HCl | 223° |
| 49 | thiophene-2-C(O)-piperazine-N-CH₂-phenyl · HCl | 236° |
| 50 | 2H-chromen-3-yl-C(O)-piperazine-N-CH₂-phenyl · HCl | 247° |
| 51 | 5-Br-benzofuran-2-C(O)-piperazine-N-CH₂-phenyl · HCl | 255° |
| 52 | thiophene-2-C(S)-piperazine-N-CH₂-thiophen-2-yl · HCl | 236° (decomposition) |
| 53 | pyridine-2-C(O)-piperazine-N-CH₂-(3-CF₃-phenyl) · HCl | 179° |
| 54 | pyridine-2-C(O)-piperazine-N-CH₂-(2,4,6-tri-CH₃-phenyl) · HCl | 213° |
| 55 | pyridine-2-C(O)-piperazine-N-CH₂-(3-F-phenyl) · HCl | 232° |
| 56 | pyridine-2-C(O)-piperazine-N-CH₂-(3,4-di-Cl-phenyl) · HCl | 225° |
| 57 | pyridine-2-C(O)-piperazine-N-CH₂-(4-OCH₃-phenyl) · HCl | 233° |
| 57 | pyridine-2-C(O)-piperazine-N-CH₂-thiophen-2-yl · HCl | 218° |

TABLE 2a-continued

| | Melting point |
|---|---|
| 58 [pyridine-C(O)-N(piperazine)N-CH₂-(thiophene) · HCl] | 218° |

TABLE 3

| Compound No. in Table 2 | UV-spectroscopy Maxima in mµ (molar extinction coefficient) | Maxima in mµ | IR-spectroscopy Acid amide bands $cm^{-1}$ | $\underset{H}{\overset{R}{\underset{|}{N^+}}}$ $Cl^-$ $cm^{-1}$ |
|---|---|---|---|---|
| 1 | 277 (18350).208 | 238 | 1628 | 2462, 2520 |
| 2 | 276 (18620).221 | 239 214 | 1640 | 2390, 2506 |
| 3 | 275 (19100) | 240 | 1644 | 2390 |
| 4 | 273 (18450) | 240 | 1622 | 2560, 2380 |
| 5 | 272 (18400) | 238 | 1640 | 2390, 2430 |
| 6 | 276 (18100).223 | 242 215 | 1640 | 2670, 2535, 2445 |
| 7 | 275 (1900) 238 | 1640 | 2500, 2394 | |
| 8 | 275 (18800) | 241 | 1640 | 2450, 2512 |
| 9 | 275 (19300).227 | 242 217 | 1620 | 2600 |
| 10 | 273 (21500) | 248 | 1635 | 2540, 2465 |
| 11 | 272 (18600).229 | 241 215 | 1652 | 2580 |
| 12 | 273 (27450) | 237 | 1637 | 2440, 2520 |
| 13 | 273 (18400).225 | 242 221 | 1655 | 2445, 2507 |
| 14 | 275 (15100) | 238 | 1640 | 2670, 2535, 2440 |
| 15 | 275 (17500) | 237 | 1622 | 2520, 2435 |
| 16 | 275 (17800).229 | 253 217 | 1640 | 2450, 2520 |
| 17 | 275 (19000) | 237 | 1640 | 2475 |
| 18 | 276 (18000) | 238 | 1646 | 2562, 2475 |
| 19 | 268 (17000) | 238 | 1628 | 2380, 2075 |
| 20 | 278 (2800).285 | 283 248 | 1645 | 2462, 2530 |
| 21 Base | 254 (15500) | 223 | 1608 | — |
| 22 Base | 254 (15900) | 238 | 1608 | — |
| 23 | 259 (1400) | 240 | 1637 | 2300 |
| 24 | no max. | no min. | 1645 | 2440 |
| 25 | 281 (515) | 279 | 1620 | 2538,2510,2440 |
| 26 | no max. | no min. | 1633 | 2700,2610 |
| 27 | 260 (11900) | 233 | 1600 | 2510,2360 |
| 28 | 232 (12000) | 218 | 1633 | 2660,2550,2460 |
| 29 | 262.5(2000).251 268.5(1700).257 | 260 246 266 253 | 1652 | 2515,2382 |
| 30 Base | 295 (17800) | 256 | 1620 | — |
| 31 | 243 (10700) | 222 | 1613 | 2520,2450 |
| 32 | 300 (20500) | 246 | — | 2520,2460 |
| 33 | 293 (15400) | 249 | — | 2380 |
| 34 | 282 (10800) | 247 | — | 2670,2590 |
| 35 | 283 (1500) | 247 | — | 2300 |
| 36 | 291 (17600).230 | 243 218 | 1618 | 2525,2450 |
| 37 | 275 (20900).318 | 243 314 | 1628 | 2500,2330 |
| 38 | 273 (19600).278 | 238 276 | 1634 | 2530,2450 |
| 39 | 273 (17800). — | 233 — | 1620 | 2540,2465 |
| 40 | 260 (20500).231 | 222 235 | 1636 | 2500,2335 |
| 41 | 240 (18500), — | — — | 1616 | 2390, — |
| 42 | 237 (19900), — | — — | 1612 | 2390, — |

TABLE 4

Starting materials for the preparation of N,N'-disubstituted cyclic diamines (the formulae of these compounds are shown in Table 5)

a) Carboxylic acid chlorides: Coumarillyl chloride, 2,3-dihydro-coumarillyl chloride, furan-2-carbonyl chloride, 2-methyl-5,6-dihydropyran-3-carbonyl chloride, 2-methyl-2,3,5,6-tetrahydropyran-3-carbonyl chloride, 2-thenoylchloride.
b) Carboxylic acid esters ethyl coumarillate, ethyl indole-2-carboxylate.
c) Carboxylic acid nitriles: Coumarillonitrile
d) N'-unsubstituted carboxylic acid piperazides: Coumarillic acid piperazide.
e) N'-substituted carboxylic acid piperazides: N-benzyl-coumarillic acid piperazide, N-benzyl-furan-2-carboxylic acid piperazide, N-benzyl-2-methyl-5,6-dihydropyran-3-carboxylic acid piperazide, N-(3,4-dichlorobenzyl)-2-methyl-5,6-dihydropyran-3-carboxylic acid piperazide.
f) Carboxylic acids: Coumarillic acid, indole-2-carboxylic acid, pyridine-4-carboxylic acid, pyridine-3-carboxylic acid, pyridine-2-carboxylic acid, thiophene-2-carboxylic acid, thiophene-3-carboxylic acid, chromen- 3-yl-3-carboxylic acid, 5-bromo-coumarillic acid.
g) Aralkylpiperazines: N-benzylpiperazine, N-(4-chlorobenzyl)-piperazine, N-(3,4-dichlorobenzyl)-piperazine, N-(2,4-dichlorobenzyl)-piperazine, N-(4-fluorobenzyl)-piperazine, N-(4-bromobenzyl)-piperazine, N-(4-methylbenzyl)-piperazine, N-mesitylmethylpiperazine, N-(4-methoxybenzyl)-piperazine, N-(3,4,5-trimethoxybenzyl)-piperazine, N-(4-hydroxybenzyl)-piperazine, N-(4-nitrobenzyl)-piperazine, N-diphenylmethylpiperazine, N-(β-phenylethyl)-piperazine, N-tetrahydrofurfuryl- 2 -piperazine, N-thenyl- 2 -piperazine, N-cyclohexylmethyl-piperazine, N-picolyl- 3 -piperazine, N-(quinolyl- 2 - methyl)- piperazine, N-(indanyl- 5 -methyl)-piperazine, N-(3-trifluoromethylbenzyl)-piperazine, N-(5-chlorothen-2-yl)-piperazine, Nβ-phenylpropyl)-piperazine, N-(2,4,6-trimethylbenzyl)-piperazine.
h) Aralkylhomopiperazines: N-benzylhomopiperazine.
i) Aralkylhalides: Benzyl chloride.
k) Amino magnesium halides: N-benzylpiperazino magnesium bromide.

TABLE 5

Starting products for the preparation of N,N'-disubstituted cyclic diamines a) Carboxylic acid chlorides TABLE 5-continued
Starting products for the preparation of N,N'-disubstituted cyclic diamines
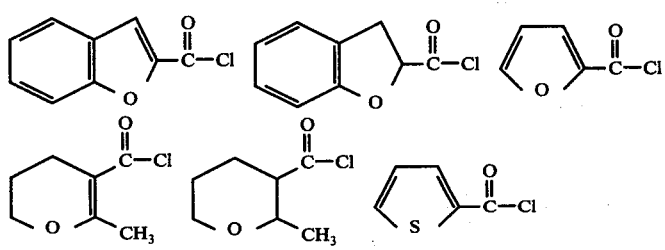
b) Carboxylic acid esters
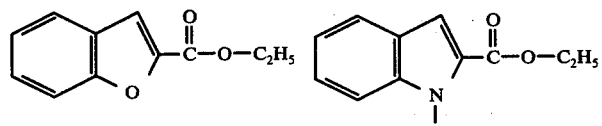
c) Carboxylic acid nitriles   d) N'-unsubstituted carboxylic acid piperazides
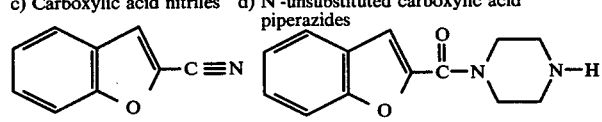
e) N'-substituted carboxylic acid piperazides
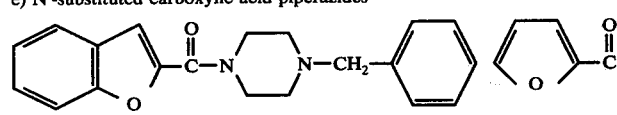
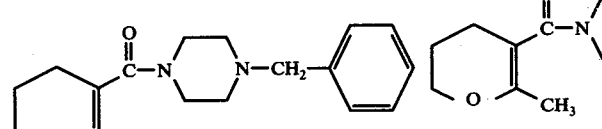
f) Carboxylic acids
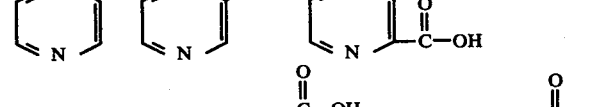
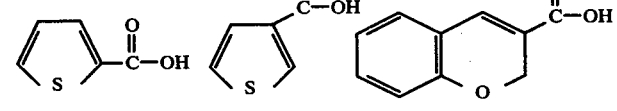
g) Aralkylpiperazines
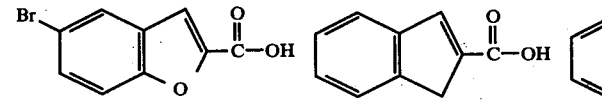
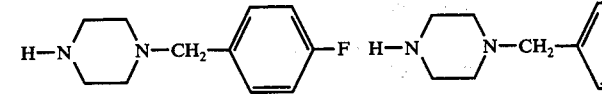

TABLE 5-continued
Starting products for the preparation of N,N'-disubstituted cyclic diamines
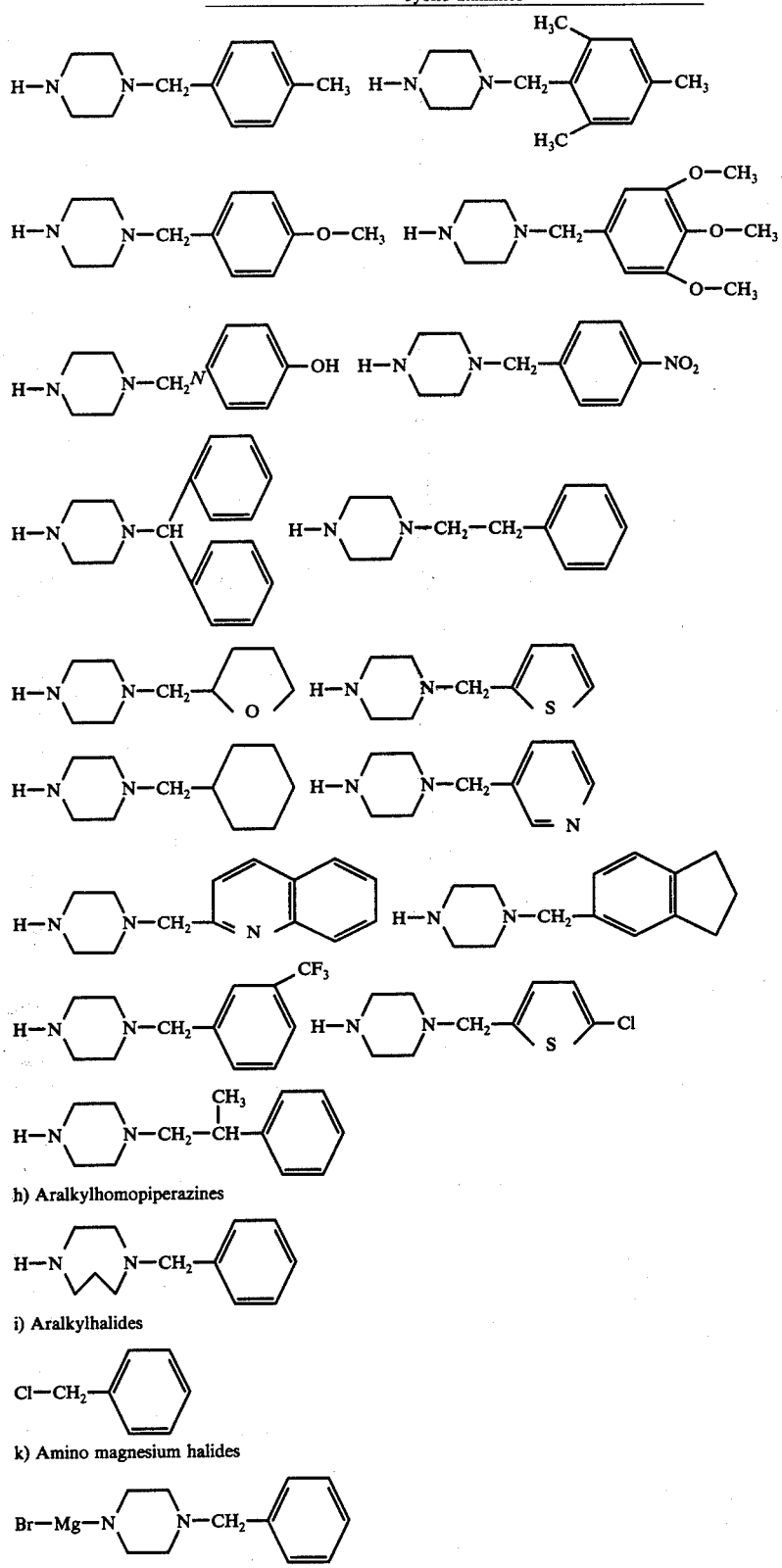
h) Aralkylhomopiperazines
i) Aralkylhalides
k) Amino magnesium halides

FORMULA SHEET
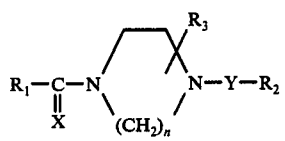
(I)
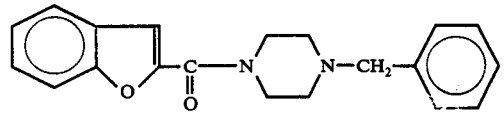
(II)
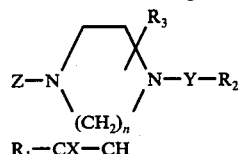
(III)
R₁—CX—CH (IV)
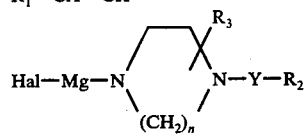
(V)
R₁—CN (VI)
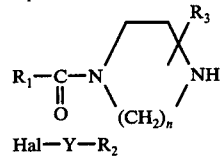
(VII)
Hal—Y—R₂ (VIII)
(IX)
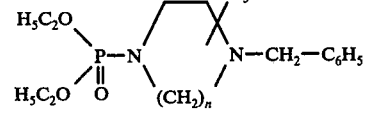
(X)
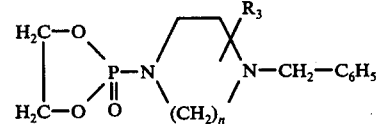
(XI)
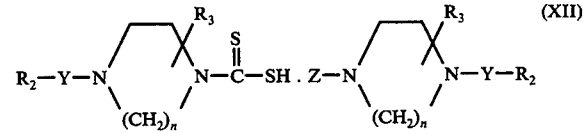
(XII)
(XIV)
R₁—C≡N
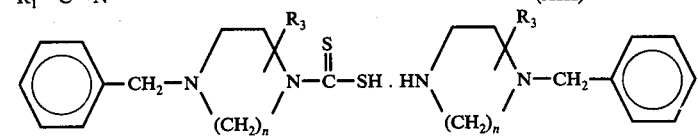
(XIII)
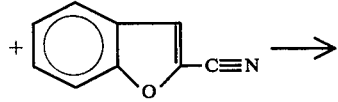
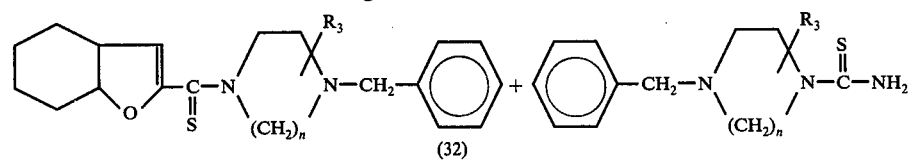
(1)

-continued

FORMULA SHEET

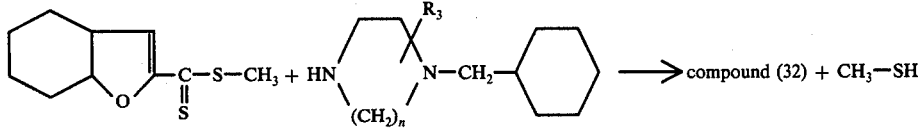

What we claim is:

1. A pharmaceutically active N,N'-disubstituted cyclic diamine compound of the formula

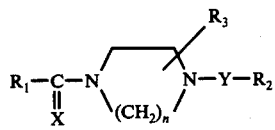

wherein
R$_1$ is an unsubstituted binuclear heterocyclic ring system bound to the group

at a carbon atom and being selected from the group consisting of benzofuryl, dihydrobenzofuryl and benzothienyl, X is oxygen, sulphur or a NH-group, Y is an unsubstituted alkylene group having 1 to 3 carbon atoms in the chain or an alkylene group having 1 to 3 carbon atoms in the chain substituted by (a) up to 3 alkyl groups each having up to 3 carbon atoms and a total of not more than 8 carbon atoms, or by (b) one or two phenyl groups, R$_2$ is a mononuclear heterocyclic radical selected from the group consisting of (A) furfuryl, tetrahydrofurfuryl and thenyl and (B) substitution products of (A) containing at least one substituent selected from the group consisting of nitro, halogen, trifluormethyl, alkyl having 1 to 6 carbon atoms, R$_3$ is hydrogen or up to two substituents selected from alkyl groups having up to 2 carbon atoms and phenyl groups;

$n$ is 2 or 3 or a physiologically-acceptable acid addition salt thereof.

2. A compound as claimed in claim 1 having the formula

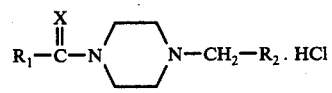

wherein the range of definitions of claim 1 R$_1$ is selected from the group consisting of

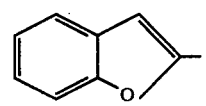

wherein X is O or S wherein R$_2$ is selected from the group consisting of

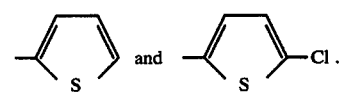

3. A compound as claimed in claim 1 wherein Y is selected from the group consisting of (a) a straight-chained unsubstituted alkylene group having up to 2 carbon atoms and (b) a substitution product of (a) being substituted by a phenyl group.

4. A compound of the formula

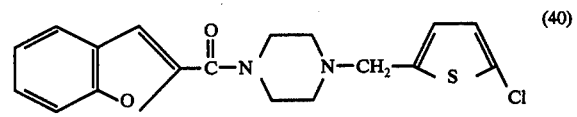

and pharmaceutically acceptable acid addition salts thereof.

5. A compound of the formula

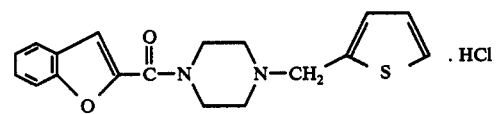

6. A pharmaceutical composition useful for psychotherapeutic treatment comprising as an active ingredient a compound (I) or its pharmaceutically acceptable acid addition salt as claimed in claim 1 together with a compatible adjuvant.

* * * * *